United States Patent [19]
Turner et al.

[11] Patent Number: 6,001,587
[45] Date of Patent: Dec. 14, 1999

[54] CHEMICALLY SPECIFIC PATTERNING ON SOLID SURFACES USING SURFACE IMMOBILIZED ENZYMES

[75] Inventors: David C. Turner, Waldorf; Bruce P. Gaber, Bethesda, both of Md.

[73] Assignee: The United States of America as represented by the Secretary of the Navy, Washington, D.C.

[21] Appl. No.: 08/841,966

[22] Filed: Apr. 8, 1997

[51] Int. Cl.$^6$ ............... C12P 1/00; C12N 11/14; C12N 11/02; C12N 11/08
[52] U.S. Cl. ............ 435/41; 435/174; 435/176; 435/177; 435/180
[58] Field of Search ............... 435/41, 174, 176, 435/177, 178, 180

[56] References Cited

U.S. PATENT DOCUMENTS

| | | | |
|---|---|---|---|
| 5,470,739 | 11/1995 | Akaike et al. | 435/402 |
| 5,602,029 | 2/1997 | Miyamoto | 435/395 |

OTHER PUBLICATIONS

A. Ashkin et al, Nature, 330, 769–771 (1987).
R. Singhvi et al, Science, 264, 696–698 (1994).
D. Turner et al, Langmuir, 12, 4411–4416 (1996).
T. E. Wilson et al, Langmuir, 10, 1512–1516 (1994).
H. Hagestam et al, J. of Chromatography, 351, 239–248 (1986).
H. Hagestam et al, Anal. Chem., 57, 1757–1763 (1985).
J. K. Whitesell et al, Angew. Chem. Int. Ed. Engl., 33, 871–873 1994.

*Primary Examiner*—David M. Naff
*Attorney, Agent, or Firm*—Thomas E. McDonnell; Barry A. Edelberg

[57] ABSTRACT

An immobilized substrate surface is chemically modified by manipulating an enzyme which is immobilized to a solid surface. Modifications include (1) chemical dissection of a substrate surface such as by chemical hydrolysis, (2) chemical synthesis on a substrate surface, and (3) chemical patterning of a substrate surface. The enzyme may be coupled to colloidal beads or particles, locally flat solid surfaces including planar, textured planar, cylindrical and spherical surfaces or arbitrary predefined shapes, or scanning probe microscope probes. In the patterning applications, colloidal particles containing the enzyme can be confined to desired regions of the substrate surface by various techniques which control the movement of the particles. The particles can be confined to tunnels or channels in a patterned polymer mold on top of the substrate surface. The enzyme can also be immobilized onto the surface of a raised pattern and this patterned surface can then be placed in contact with the immobilized substrate.

18 Claims, 4 Drawing Sheets

CHEMICALLY SPECIFIC PATTERNING ON SOLID SURFACES USING SURFACE IMMOBILIZED ENZYMES

BACKGROUND OF THE INVENTION

1. Field of the Invention

This invention relates to an enzyme-substrate system where both the enzyme and substrate are immobilized to solid surfaces and the immobilized enzyme is manipulated such that it can chemically modify the immobilized substrate surface.

2. Description of the Previously Published Art

Many approaches exist for immobilization of enzymes on solid surfaces. Enzymes have been covalently immobilized on chromatography supports for use as a chemically active chromatography column for detecting and/or modifying enzyme substrates passing through the column as described by P. Jadaud et al, J. Chromotography, 476, 165–174 (1989). Alternatively, immobilized enzymes have been used in assays for calorimetric detection of analytes such as the ELISA assay as described by D. J. Reen, Methods in Molecular Biology, 32, 461–6 (1994). As a result of these two technologies, a wide variety of immobilization chemistries have been developed which may be used to maximize the activity of the immobilized enzyme in question. Thus, the art of enzyme immobilization is a mature technique which provides a strong base on which to build this new technology.

In a manner similar to enzyme immobilization, the immobilization of enzyme substrate materials which are capable of reacting with enzymes such as peptides, proteins, lipids, carbohydrates and nucleic acids has been widely studied by many and the following three are just illustrative of that work: Vandenberg et al, J. Colloid Interface Sci, 143, 327–335 (1991); H. Lang et al, Langmuir, 10, 197–210 (1994); and S. Britland et al, Biotechnol. Prog., 8, 155–160 (1992). There have also been several reports which described solution enzyme modification of (solid surface) immobilized substrates as exemplified by T. E. Wilson et al, Langmuir, 10, 1512–1516 (1994) and I. H. Hagestam et al, J. Chromotography, 351, 239–248 (1986). There are no reports, however, indicating that solution phase enzymes have been used to make chemical patterns on substrate surfaces.

Many techniques have been developed for modification and patterning of solid surfaces. These range from conventional lithography utilizing photoresists (including electron and ion beams) as described in the book *Semiconductor Lithography* by W. Moreau, Plenum Press, New York, (1988); patterning of self-assembled monolayer and silane ultrathin films as described by J. M. Calvert, J. Vac. Sci. Technol., B11, 2155–2163 (1993) and A. Kumar et al, Langmuir, 10, 1498–1511 (1994); and a variety of patterning approaches using scanning probe microscopes as described in *The Technology of Proximal Probe Lithography*, C. R. K. Marrian, Ed, SPIE Volume IS10, SPEE Press, Bellingham, Wash. (1993). Some of these approaches do exhibit a degree of chemical selectivity (mainly by absorbing photons of specific energy) as seen by the Moreau and Calvert publications, however, none show the spectrum of chemical selectivity possible with enzyme controlled modification. In addition, conventional photoresist patterning requires harsh chemical conditions (organic solvents, elevated temperature) to develop the patterns. Both conventional photoresist and ultrathin film resists require intense photon sources or electron/ion sources to carry out the patterning.

3. Objects of the Invention

It is an object of this invention to provide chemically specific modification of surfaces in a controlled manner.

It is a further object of this invention to provide chemically specific modification of surfaces based on enzyme based catalysis chemistry which uses environmentally benign reaction conditions.

It is a further object of this invention to provide chemical dissection of a surface where the catalytic reactants can be quickly and easily recovered via filtration without fouling the system or the surface.

It is a further object of this invention to provide chemical dissection of a surface by chemical hydrolysis.

It is a further object of this invention to provide chemical modification of a surface where several enzymes could be used on the same substrate to carry out different types of chemically specific modifications.

It is a further object of this invention to provide for a complex series of chemical steps that can be carried on a surface without introduction of harsh solvents or conditions.

It is a further object of this invention to conduct environmentally friendly surface synthesis via enzyme catalyzed chemical reactions.

It is a further object of this invention to provide chemically specific synthesis of surfaces based on enzyme based catalysis chemistry which uses environmentally benign reaction conditions.

It is a further object of this invention to provide chemically-specific patterning and modification of surfaces.

It is a further object of this invention to create complex chemical patterns on a surface.

It is a further object of this invention to provide chemically specific patterning and modification of surfaces based on enzyme based catalysis chemistry which uses environmentally benign reaction conditions.

It is a further object of this invention to create complex chemical patterns on a surface without the use of harsh solvents or conditions.

It is a further object of this invention to create complex chemical patterns on a surface with an enzyme scheme which takes place in an aqueous environment without the need for harsh conditions like organic solvents, high energy beams, or extreme temperature.

It is a further object of this invention to conduct chemical patterning to take place with high chemical selectivity and without ancillary damage to surrounding surface components or the solid substrate material.

It is a further object of this invention to manipulate the position of a single bead coated with immobilized enzymes for high resolution patterning of substrate surfaces.

It is a further object of this invention to place immobilized enzymes on a solid surface which would then be used as a chemical stamp to allow rapid reproduction of a complex pattern on many substrate surfaces.

These and further objects of the invention will become apparent as the description of the invention proceeds.

SUMMARY OF THE INVENTION

This invention covers any enzyme-substrate system where both the enzyme and substrate are immobilized to solid surfaces and the immobilized enzyme is manipulated such that it can chemically modify the immobilized substrate surface. This includes the use of such a system for chemical dissection of a substrate surface such as by chemical hydrolysis, for chemical synthesis on a substrate surface, and for chemical patterning of a substrate surface. The enzyme may be coupled to colloidal beads or particles, locally flat solid surfaces including planar, textured planar, cylindrical and spherical surfaces or arbitrary predefined shapes, or scanning probe microscope probes. For patterning applications using colloidal particles there are several ways to confine the particles to desired regions of the substrate surface. For example, it may be possible to position the particles mechanically by using micromanipulators, by an optical trap, or by using EM fields with charged or magnetic particles. One may also confine the particles to tunnels or channels in a patterned polymer mold on top of the substrate surface. The enzyme can also be immobilized on to the surface of a raised pattern and this patterned surface can then be placed in contact with the immobilized substrate.

DESCRIPTION OF THE PREFERRED EMBODIMENTS

This technique is designed to allow chemically specific patterning and modification of surfaces. In addition, because the chemistry is due to enzyme based catalysis, the approach is applicable using environmentally benign reaction conditions (aqueous solutions). Since enzyme immobilization chemistry is known for a wide variety of surfaces, this technique has many possible implementations. For example, enzymes immobilized on colloidal beads can be used for specific chemical modification of a surface and then be quickly and easily recovered via filtration without fouling the system or the surface. In this way, a complex series of chemical steps could be carried out on the surface without introduction of harsh solvents or conditions. This could be a useful way to conduct environmentally friendly surface synthesis.

Alternatively, the spatial distribution of the colloidal beads could be restricted such that the surface chemistry is modified only in predefined spatial locations. This allows one to create complex chemical patterns on a surface without the use of harsh solvents or conditions. Moreover, the patterning takes place with high chemical selectivity and without ancillary damage to surrounding surface components or the solid substrate material.

As to enzymes immobilized on beads, one could manipulate the position of a single bead for high resolution patterning of substrate surfaces. This approach has the potential for molecular scale (<about 1 nm) feature size resolution. Suitable ways to manipulate a single bead include attachment to an atomic force microscope (AFM) tip or grabbing a bead with an optical trap (tweezer). An optical trap, which is also known as optical tweezers, is a relatively new optical technique which can be used to manipulate micron to mm size particles. See, for example, A. Ashkin et al, Nature, 330, 769–771 (1987). It should be noted also that enzymes could be directly immobilized to an AFM probe.

Figure 1:
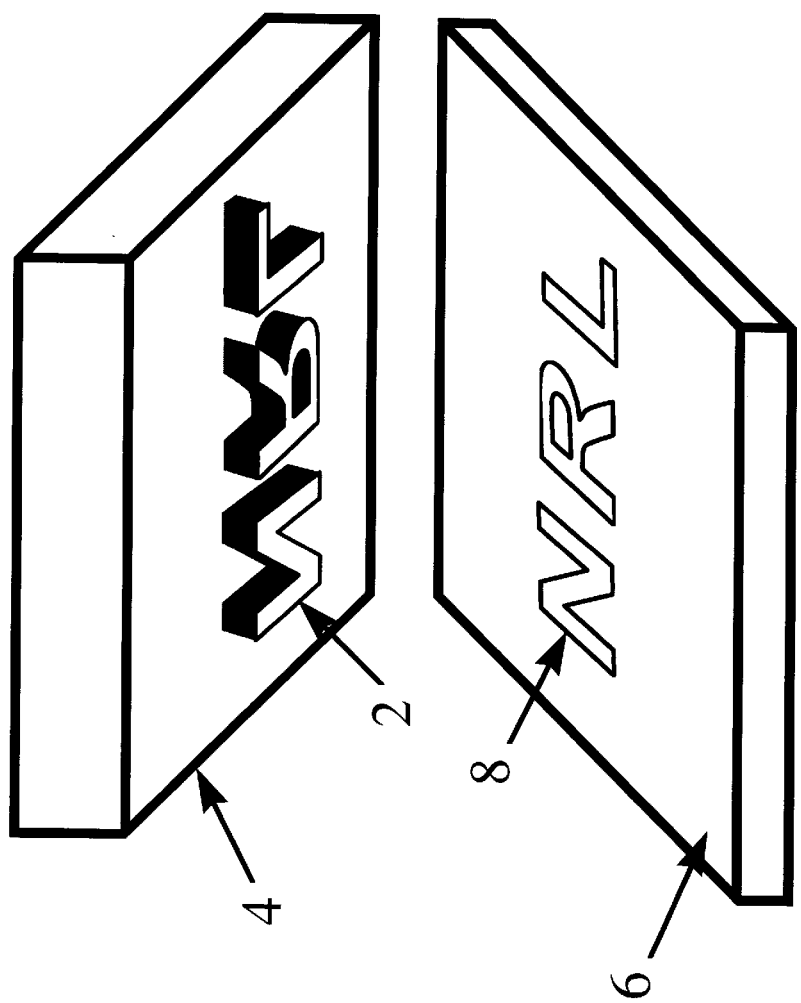
FIG. 1 illustrates a chemical stamp.

Finally, enzymes could be immobilized on solid surfaces which would then be used as chemical stamps in the manner of the Whitesides et al. alkylthiol stamp described by R. Singhvi et al, Science, 264, 696–698 (1994). See FIG. 1 where the raised image 2 on the upper surface 4 can have a coating of the enzyme. When this stamp is contacted with the immobilized substrate 6 below, a pattern corresponding to the image 2 will be formed as 8. This would allow rapid reproduction of a complex pattern on many substrate surfaces.

Compared with patterning and surface modification schemes described in the prior art, the immobilized enzyme-based approach for chemical modification and patterning has at least three possible advantages.

First is the high degree of chemical selectivity possible using enzyme modification. One can choose an appropriate enzyme with which very specific chemistry can be carried out on the substrate. In fact, several enzymes could be used on the same substrate to carry out different types of chemically specific modification. Appropriate enzymes for use with the present invention include, for example, proteases, lipases, esterases, hydrolases, and RNAases.

Second, the enzyme scheme takes place in an aqueous environment without the need for harsh conditions like organic solvents, high energy beams, or extreme temperature.

Third, by using a single enzyme it may be possible to modify substrate surfaces with nearly molecular scale resolution ($\geq 1$ nm). This could be accomplished either by immobilizing a single enzyme to an AFM tip for serial pattern writing or by making a stamp with single enzyme line resolution which could be used for parallel (i.e. rapid) pattern writing.

Some alternative implementations of this system are possible. They include: any other immobilized enzyme/immobilized substrate system, immobilization of the enzyme on colloidal particles of any type, enzymes immobilized on a solid surface in a pattern for chemically patterning an immobilized substrate on a solid surface, and enzyme immobilization on a scanning probe microscope tip for substrate patterning applications.

This invention could find applications in the biotech industry for making multiple analyte biosensors and for high resolution lithography.

Having described the basic aspects of the invention, the following examples are given to illustrate specific embodiments thereof.

EXAMPLE 1

This example illustrates the operability of an enzyme chemisorbed on a solid bead being able to chemically modify a fluorescent peptide substrate.

The chemisorbed fluorescent peptide substrate chosen was succinic acid-alaninealanine-phenylalanine-aminomethylcoumarin (SUC-ALA-ALA-PHE-AMC or SAAP-AMC). This SAAP-AMC was immobilized to aminosilane modified silica substrates by forming an amide bond between the carboxylic acid group on the peptide (on the succinic acid) and the primary amine on the aminosilane surface.

SAAP-AMC fluoresces at 395 nm when excited with 325 nm light. If the AMC group is cleaved from the SAAP-AMC, then in solution the AMC fluorescence shifts to a wavelength of 445 nm when excited at 345 nm. Thus it is an ideal probe for the activity of the presence of an enzyme which can cleave the AMC group.

One of the enzymes which can cleave the AMC group is α-chymotrypsin and this enzyme can be chemisorbed to silica or acrylic beads.

Figure 2:
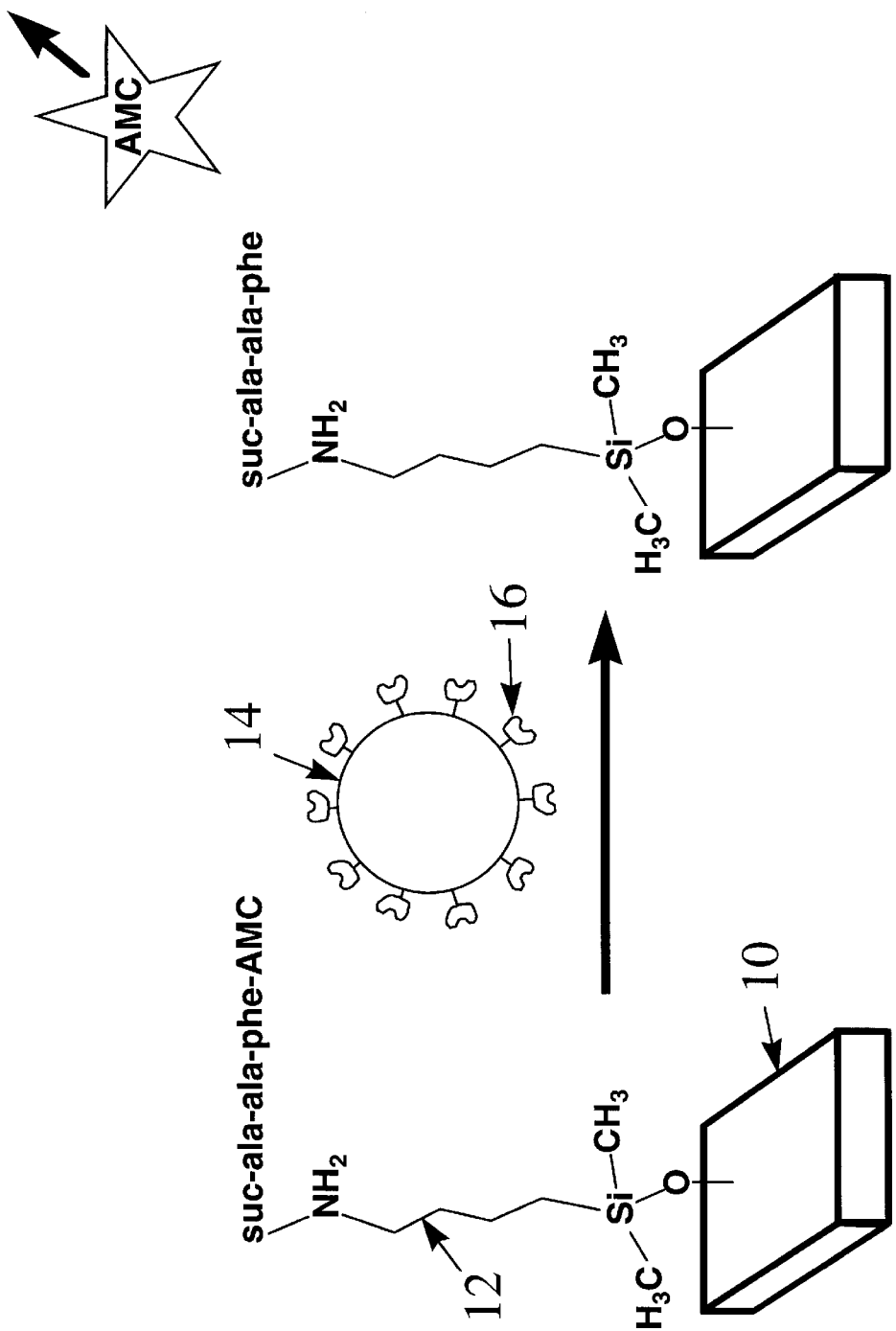
FIG. 2 illustrates a bead with the α-chymotrypsin cleaving off an AMC group.

The overall reaction is schematically illustrated in FIG. 2 where the chymotrypsin bead modifies the SAAP-AMC group. The silica substrate 10 has attached an aminosilane group which is conjugated to the SAAP-AMC as indicated by 12. The silica bead 14 has the chymotrypsin molecule 16 covalently coupled to the silica bead. As the bead contacts the SAAP-AMC group, the AMC group is released as seen on the right side of the figure.

As to the experimental procedure, first the materials were checked to make sure they react according to theory. Fluorescence is emission from the immobilized peptide surfaces was observed at 395 nm using an SLM/AMINCO 8000 fluorimeter with an excitation wavelength of 325 nm as expected. When the SAAP-AMC surface was treated with α-chymotrypsin in solution the fluorescence from the surface (at 395 nm) decreased with enzyme dose while the fluorescence in solution (at 445 nm) increased. Removal of the AMC group from the surface was complete after several hours which indicates the good activity of the solution phase α-chymotrypsin for the immobilized peptide surface.

The next step is to determine whether α-chymotrypsin chemisorbed on a solid bead will also have good activity for the immobilized peptide surface.

Figure 3:
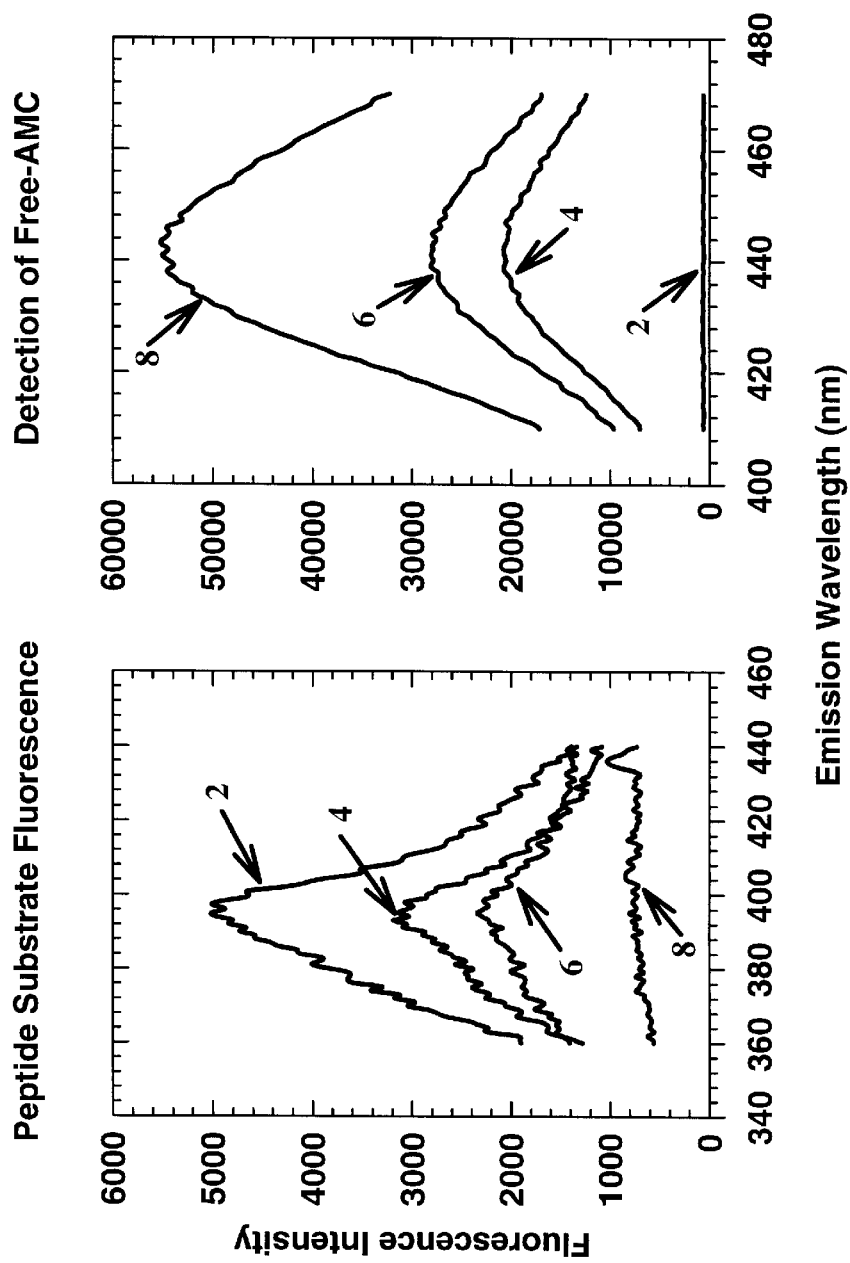
FIG. 3 illustrates the fluorescence as a function of α-chymotrypsin treatment time.

The beads were prepared by reacting aminosilane modified 250 nm silica spheres with glutaraldehyde. Then α-chymotrypsin was immobilized on the bead by reaction with the glutaraldehyde. Finally, the enzyme coated spheres were treated with EGS (ethylene glycobis (succinimidylsuccinate)) to stabilize the enzyme attachment to the bead surface. After the beads were rinsed carefully in buffered detergent to remove any unbound α-chymotrypsin, the bead suspension was placed on the immobilized SAAP-AMC surfaces for up to 24 hrs. The fluorescence of the α-chymotrypsin treated SAAP-AMC slides was investigated as a function of time. FIG. 3 illustrates the fluorescent spectra of SAAP-AMC peptide surface on the left side and supernatant solution on the right side as a function of time of treatment with chymotrypsin modified silica beads. The legend for the curves is that line 2 is at time zero, line 4 is after 10 minutes, line 6 is after one hour and line 8 is after 12 hours. The enzymatic activity removes the fluorescence AMC group from the peptide surface and releases it into solution resulting in a decrease in fluorescence from the surface and an increase in fluorescence in the solution above the surface. As seen in FIG. 3, the surface fluorescence of the peptide substrate at 395 nm on the left side decreased concomitantly with an increase of fluorescence at 445 nm on the right side as the AMC was released into solution. After 24 hours, no fluorescence was observed from the peptide surface. This demonstrated that the immobilized α-chymotrypsin was active on the immobilized SAAP-AMC substrate and was able to entirely remove the AMC from the surface.

EXAMPLE 2

This example illustrates the chemical patterning which is obtained by directing α-chymotrypsin beads to float over regions of an immobilized SAAP-AMC surface.

Figure 4:
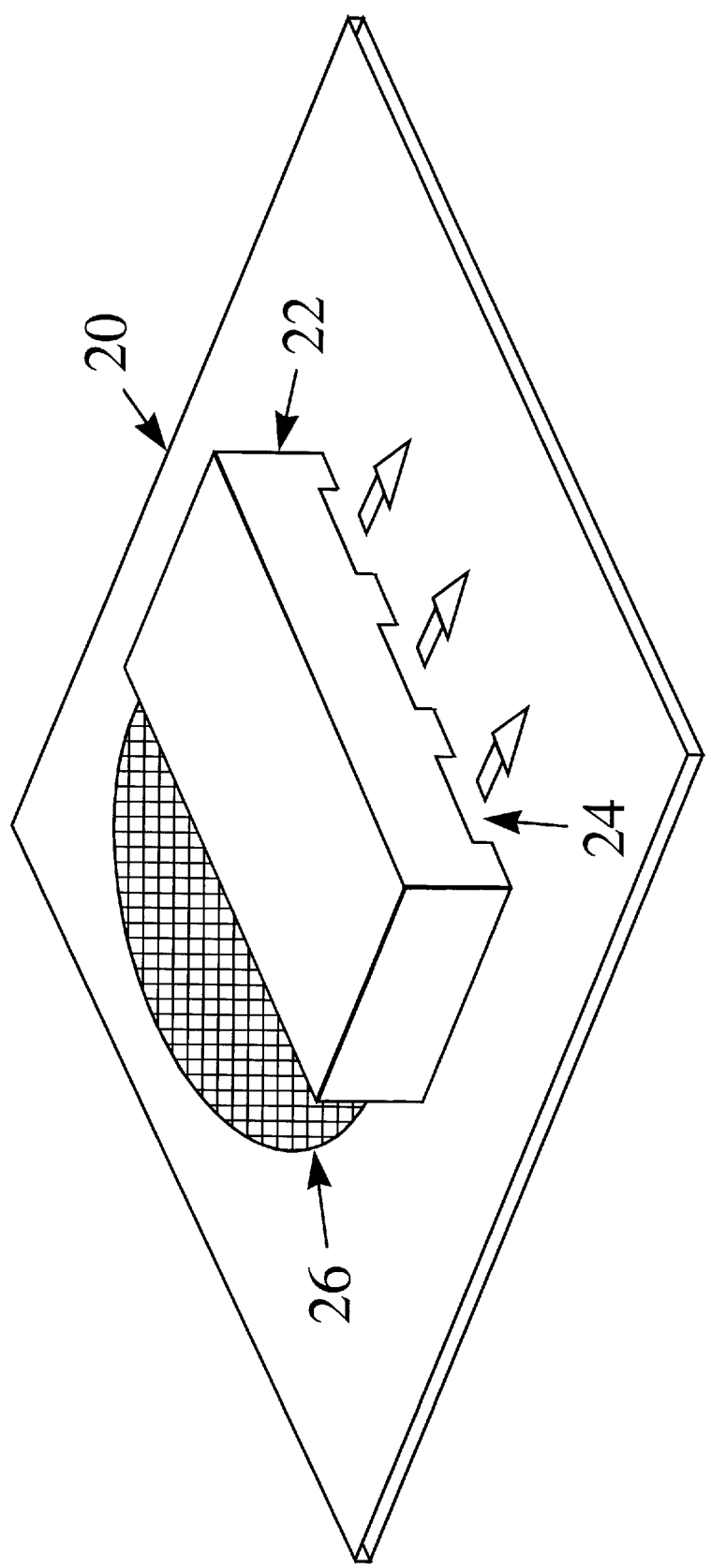
FIG. 4 illustrates a mold for channel patterning.

As illustrated in FIG. 4, an immobilized SAAP-AMC surface 20 was contacted with a polydimethylsiloxane (PDMS) polymer mold 22 which was placed over the surface. The mold has channels 24 in the mold which extend over the surface. A solution 26 containing α-chymotrypsin beads was permitted to flow through these channels by a wicking action and over the surface. After several hours the PDMS mold was removed and the substrate was thoroughly rinsed. Lateral force AFM images showed line patterns as expected indicating that chemical patterning had taken place.

Control experiments using a buffer, but with no beads flowing through the PDMS channels, showed no evidence of patterning.

To further confirm that α-chymotrypsin was removing the AMC group from the peptide surface and leaving a free carboxylic acid group behind, a fluorophore was reacted with the peptide surface after the bead treatment. Fluorescene isothiocyanate (FITC) labeled cadaverine was attached to the free carboxyl group left after the enzyme hydrolysis via amide bond formation. Fluorescence microscopy shows the selective attachment of the fluorescent cadaverine to regions of the SAAP-AMC substrate which were exposed to the α-chymotrypsin beads (i.e. the areas within the channels).

It is understood that the foregoing detailed description is given merely by way of illustration and that many variations may be made therein without departing from the spirit of this invention.

What is claimed is:

1. A method for chemically modifying an immobilized substrate surface comprising
   a) providing a substrate which is immobilized to a solid surface;
   b) providing an enzyme which is immobilized to another solid surface and which chemically reacts with the substrate; and
   c) manipulating the enzyme on the solid surface in contact with the substrate so that it chemically modifies the substrate.

2. A method according to claim 1, wherein the manipulation produces a chemical lysis of the substrate surface.

3. A method according to claim 1, wherein the manipulation produces a chemical synthesis on the substrate surface.

4. A method according to claim 1, wherein the manipulation produces a chemical patterning of the substrate surface.

5. A method according to claim 4, wherein the manipulation produces either a chemical lysis on the substrate surface or a chemical synthesis on the substrate surface.

6. A method according to claim 4, wherein the enzyme is immobilized onto particles.

7. A method according to claim 6, wherein the manipulation produces a chemical patterning of the substrate surface by confining the particles to desired regions of the substrate surface.

8. A method according to claim 7, wherein the enzyme is coupled to colloidal particles.

9. A method according to claim 8, wherein the colloidal particles are positioned either by mechanically using micromanipulators, by using an optical trap, or by using EM fields with charged or magnetic particles.

10. A method according to claim 7, wherein the particles are confined to tunnels on top of the substrate surface by using patterned polymer molds having tunnels therein.

11. A method according to claim 4, wherein said solid surface to which said enzyme is immobilized is a single bead, and wherein said single bead is manipulated for high resolution patterning of substrate surfaces.

12. A method according to claim 11, wherein the single bead is manipulated by attachment to an atomic force microscope (AFM) tip or grabbing a bead with an optical trap.

13. A method according to claim 4, wherein the enzyme is immobilized onto the surface of a raised pattern and this patterned surface is placed in contact with the immobilized substrate.

14. A method according to claim 1, wherein the enzyme is coupled to a solid surface selected from the group consisting of colloidal particles, locally flat solid surfaces, and scanning probe microscopes probes.

15. A method according to claim 1, wherein the substrate is selected from the group consisting of peptides, proteins, lipids, carbohydrates and nucleic acids.

16. A method according to claim 1, wherein the enzyme is selected from the group consisting of proteases, lipases, esterases, and RNAases.

17. The method of claim 1, wherein said enzyme is a hydrolase.

18. The method of claim 1, wherein said solid surface to which said enzyme is coupled is a colloidal bead.

* * * * *